US008043862B2

United States Patent
Solazzi (10) Patent No.: US 8,043,862 B2
(45) Date of Patent: *Oct. 25, 2011

(54) SAMPLE CUP FOR USE WITH X-RAY SPECTROSCOPY WITH INTERNAL OVERFLOW RESERVOIR

(75) Inventor: Monte J. Solazzi, Palm City, FL (US)

(73) Assignee: Chemplex Industries, Inc., Palm City, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/925,048

(22) Filed: Oct. 13, 2010

(65) Prior Publication Data

US 2011/0051134 A1  Mar. 3, 2011

Related U.S. Application Data

(63) Continuation-in-part of application No. 12/658,887, filed on Feb. 17, 2010, which is a continuation of application No. 10/990,994, filed on Nov. 17, 2004, now Pat. No. 7,722,821.

(51) Int. Cl.
    *G01N 21/76* (2006.01)
(52) U.S. Cl. ........ 436/172; 436/171; 422/500; 422/547; 422/557; 422/561; 206/527; 378/45; 378/47; 378/79; 378/208; 73/864.91
(58) Field of Classification Search .................. 422/500, 422/547, 557, 561; 378/208, 45, 47, 49; 73/864.91; 436/171, 172; 356/246
See application file for complete search history.

(56) References Cited

U.S. PATENT DOCUMENTS

| | | |
|---|---|---|
| D238,693 S | 2/1976 | Solazzi |
| 4,409,854 A | 10/1983 | Solazzi |
| 4,448,311 A | 5/1984 | Houser |
| 4,575,869 A | 3/1986 | Torrisi et al. |
| 4,643,033 A | 2/1987 | Solazzi |
| 4,665,759 A | 5/1987 | Solazzi |
| 4,698,210 A | 10/1987 | Solazzi |
| 4,974,244 A | 11/1990 | Torrisi |
| 4,986,965 A | 1/1991 | Ushikubo |
| 5,253,280 A | 10/1993 | Mizuta |
| 5,323,441 A | 6/1994 | Torrisi |
| 5,451,375 A | 9/1995 | Solazzi |
| 5,454,020 A | 9/1995 | Solazzi |
| 5,630,989 A | 5/1997 | Solazzi |
| 6,603,544 B1 | 8/2003 | Eckert |

*Primary Examiner* — In Suk Bullock
*Assistant Examiner* — Dennis M White
(74) *Attorney, Agent, or Firm* — Keene IP Law (57) ABSTRACT

A sample cup for retaining a sample material to be subjected to an x-ray spectrochemical analysis. The sample cup comprises a cell body of a cylindrical configuration having an open top end and an open bottom end and defining a hollow between the two open ends, the open top end having an outer wall and an inner wall encircling the open top end. The outer wall and the inner wall extend axially and are positioned in concentric relationship with one another and form an internal reservoir space therebetween.

19 Claims, 10 Drawing Sheets

SAMPLE CUP FOR USE WITH X-RAY SPECTROSCOPY WITH INTERNAL OVERFLOW RESERVOIR

RELATED APPLICATIONS

This application is a continuation-in-part of, and claims priority from, application Ser. No. 12/658,887, filed on Feb. 17, 2010, which is a continuation of application Ser. No. 10/990,994, filed on Nov. 17, 2004, now U.S. Pat. No. 7,722,821, the entire contents of each of which are hereby incorporated by reference herein.

FIELD OF THE INVENTION

The present invention relates to an x-ray spectroscopy sample container cup having an internal reservoir for accommodating sample overflows.

BACKGROUND OF THE INVENTION

Spectroscopy is a science where a sample substance is analyzed by means of the spectra of light the sample absorbs or emits. Technological advancements in both wavelength-dispersive (WD-XRF) and energy-dispersive (ED-XRF) X-ray fluorescence instrumentation enable the spectroscopic analysis of virtually all types of sample materials. In this technology, sample cups or sample receptacles are employed to hold or contain liquid, solid and powdered specimens. Many conventional prior art sample cups consist of four components. The four components include a cell body with at least one open end; a thin film of material capable of covering the open end of the cell body; an annular collar used to pull the thin film of material taut over the open end of the cell body; and a snap-on retainer ring used to secure the thin film of material in place. The thin film of material encloses a sample substance within the cell body and provides a sample surface plane which is exposed to an excitation source, such as an X-ray tube, during the analysis. Such conventional prior art cups are exemplified by U.S. Pat. No. Des. 238,693 entitled "CELL FOR X-RAY SPECTROSCOPY OR SIMILAR ARTICLE" issued on Feb. 3, 1976 to Monte J. Solazzi; U.S. Pat. No. 4,409,854 entitled "SAMPLE CUP WITH VENTING MEANS FOR USE IN X-RAY SPECTROSCOPY" issued on Oct. 18, 1983 to Michael C. Solazzi; U.S. Pat. No. 4,643,033 entitled "SAMPLE CUP FOR USE IN X-RAY SPECTROSCOPY" issued on Feb. 17, 1987 to Monte J. Solazzi; U.S. Pat. No. 4,665,759 entitled "SAMPLE CUP WITH A CANTILEVER BEAM VENTING MEANS" issued on May 19, 1987 to Monte J. Solazzi; U.S. Pat. No. 4,698,210 entitled "SAMPLE CUP APPARATUS FOR USE IN X-RAY SPECTROSCOPY EMPLOYING SELECTIVELY OPERATED VENTING MEANS" issued on Oct. 6, 1987 to Michael C. Solazzi; U.S. Pat. No. 5,451,375 entitled "APPARATUS FOR TRIMLESS SAMPLE CUP USED IN X-RAY SPECTROSCOPY" issued on Sep. 19, 1995 to Monte J. Solazzi; U.S. Pat. No. 5,454,020 entitled "SAMPLE CUP ADAPTED FOR UPRIGHT HORIZONTAL AND INCLINED SAMPLE PLANE GEOMETRY SYSTEMS" issued on Sep. 26, 1995 to Monte J. Solazzi; and U.S. Pat. No. 5,630,989 entitled "APPARATUS FOR TRIMLESS SAMPLE CUP USED IN X-RAY SPECTROSCOPY" issued on May 20, 1997 to Monte J. Solazzi.

During spectrochemical analysis it is essential for the surface of thin film material, which covers an open top of the cell body, to remain planar in order to produce reliable data. The area of the thin film material that covers the top of the cell body is known as the sample surface plane. During the spectrochemical analysis of certain specimens that exhibit high abrogation in air, the sample cup containing a specimen may be placed within a vacuum or inert gas environment. Under conditions where pressure equalization is not implemented, the thin film of material covering the sample will distend or bow outwardly due to the differential in pressures between the area within the sample cup and the environment surrounding the sample cup, which effect places portions of the thin film of material closer to the source of excitation. The variation in distance from the sample plane to the source of excitation, alters the intensity of the characteristic radiation of the specimen and also alters the intensity of radiation impinging upon the sample specimen from the excitation source. Consequently, the spectrochemical analysis may produce erroneous quantitative data. For applications in a gaseous environment where pressure is greater on the outside of the sample cup than within the sample cup, the thin film of material distends or is drawn into the hollow of the sample cup providing a concave sample surface, which effect increases the distance between the sample plane and the excitation source and results in erroneous analytical data.

In order to equalize pressure and eliminate distension of the sample surface plane, some sample cups are provided with a venting means. The venting means may be activated to provide pressure equalization between the inside and outside of the cup. Other sample cup designs include a main cell component with both ends opened. This double open-ended cup allows for attachment of the thin film sheet prior to the introduction of the sample. This design is useful for applications in an environment where continuous venting is desired from the moment of sample introduction.

In some situations, the spectroscopic analysis may be conducted in a vacuum or pressurized inert gas environment. In order to equalize the pressure between the inside and outside of the sample cups, some of these prior art sample cups have a vent hole. In addition, those prior art sample cups with the vent hole have the reservoir space on the exterior surface of the sample cups for catching any specimen material that may overflow out of the vent holes. However, because these reservoir spaces are provided on a cap or a cap-like structure that encloses the sample cup, if the sample cup is to be left open during the spectrochemical analysis without the cap, the reservoir is no longer available.

Thus, there is a need for an improved sample cup that may be placed in the spectrochemical analysis chamber with its top end open and still having a reservoir space to accommodate overflowing sample material during the spectrochemical analysis.

SUMMARY OF THE INVENTION

According to an aspect of the present invention, a sample cup for retaining a specimen to be subjected to spectrochemical analysis is disclosed. The sample cup comprises a cell body of a cylindrical configuration having an open top end and an open bottom end and defining a hollow between the two open ends. The open top end has an outer wall and an inner wall encircling the open top end. The outer wall and the inner wall extend axially and are positioned in concentric relationship with one another and form a reservoir space between them. The sample cup further comprises a means for covering the opened bottom end of the cell body when a specimen is contained within the hollow.

According to another aspect of the invention, a sample cup for retaining a specimen to be subjected to analysis includes a substantially cylindrical cell body including an open top end including an outer wall with an outer top edge and an inner wall with an inner top edge, the outer wall and said inner wall extending axially and positioned in a concentric relationship, the outer wall and said inner wall forming an internal reservoir space therebetween for receiving overflow of an expanded sample material; an open bottom end; and a hollow defined between the open top end and the open bottom end for receiving a sample material capable of expansion during analysis, the inner wall allowing the expanded sample material to flow downwardly over the inner top edge and the outer top edge preventing overflow of the expanded sample material out of the cell body.

According to another aspect of the invention, a sample cup assembly for retaining a specimen to be subjected to analysis includes a substantially cylindrical cell body including an open top end including an outer wall with an outer top edge and an inner wall with an inner top edge, the outer wall and the inner wall extending axially and positioned in a concentric relationship, the outer wall and the inner wall forming an internal reservoir space therebetween for receiving overflow of an expanded sample material; an open bottom end; and a hollow defined between the open top end and the open bottom end for receiving a sample material capable of expansion during analysis, the inner wall allowing the expanded sample material to flow downwardly over the inner top edge and the outer top edge preventing overflow of the expanded sample material out of the cell body; a thin film of material disposed across the open bottom end; and means for retaining the thin film of material tautly across the open bottom end.

According to another aspect of the invention, a method for spectroscopically analyzing a sample material includes the steps of: disposing a sample material into a sample cup, including a substantially cylindrical cell body that includes an open top end including an outer wall with an outer top edge and an inner wall with an inner top edge, the outer wall and the inner wall extending axially and positioned in a concentric relationship, the outer wall and the inner wall forming an internal reservoir space therebetween for receiving overflow of an expanded sample material; an open bottom end; and a hollow defined between the open top end and the open bottom end for receiving a sample material capable of expansion during analysis, the inner wall allowing the expanded sample material to flow downwardly over the inner top edge and the outer top edge prevents overflow of the expanded sample material out of the cell body; and subjecting the sample material to spectroscopic analysis.

When conducting a spectrochemical analysis on a sample that heats up from excitation by the X-ray and therefore expands during the analysis, the reservoir space formed between the concentric inner and outer walls will hold the overflowing sample material and prevent it from spilling over into the spectrochemical analysis sample chamber. Inadvertent spillage into the x-ray analytical system is thereby avoided together with the time-consuming decontamination clean-ups.

Alternatively, rather than accommodating overflowing sample material, the inner wall of the cell body may be used to ensure that a predetermined quantity of sample is dispensed into the sample cup. The height of the inner wall of the cell body may be set equal to the height of the sample material equating to a predetermined quantity of the sample. Any excess sample material dispensed into the sample cup will overflow into the reservoir space.

In one preferred embodiment, the inner wall of the open top end is shorter than the outer wall of the open top end such that the expanding specimen material can flow over the inner wall into the reservoir space and the taller outer wall prevents the specimen from spilling out of the sample cup.

The means covering the open bottom end of the cell may comprise a thin sheet of polymer stretched over the open bottom end and a snap-on retaining ring positioned about an outer edge of the cell body near the open bottom end to hold the thin sheet of polymer in place.

Alternatively, the means may comprise a thin sheet of polymer stretched over the open bottom end; and an annular collar positioned about an outer surface of the cell body to hold the thin sheet of polymer in place.

In one aspect, the cell body has a peripheral groove around an outer surface thereof and located nearer the open bottom end to cooperate with and retain the snap-on retaining ring. The snap-on retaining ring has an inwardly extending peripheral ridge about its top opening and adapted to cooperate with the peripheral groove in the cell body achieving a snap-fit arrangement to securely hold the thin sheet of polymer between the cell body and the snap-on retaining ring.

In one aspect, the sample cup according to another embodiment of the present invention may include a friction-fitting cap member for sealing the open top end of the cell body after the specimen is placed inside the sample cup. The cap member may have a circular disk-like shape having a top surface and a bottom surface. One or more peripherally disposed sidewall extends downwardly from the bottom surface of the cap. The sidewall frictionally engages the inner surface of the outer wall for sealing the top end opening of the cell body.

In another aspect of the invention, the cell body includes an annular recess on the outer wall surface for receiving a cap that frictionally engages with the outer wall surface of the cell body.

BRIEF DESCRIPTION OF THE DRAWINGS

The features shown in the above referenced drawings are not intended to be drawn to scale nor are they intended to be shown in precise positional relationship. Like reference numbers indicate like elements.

DETAILED DESCRIPTION OF THE INVENTION

The terms "a" or "an" as used herein are to describe elements and components of the invention. This is done merely for convenience and to give a general sense of the invention. The description herein should be read to include one or at least one and the singular also includes the plural unless indicated to the contrary.

The term "comprises", "comprising", "includes", "including", "as", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present) and B is false (or not present); A is false (or not present) and B is true (or present); and both A and B are true (or present).

Figure 1:
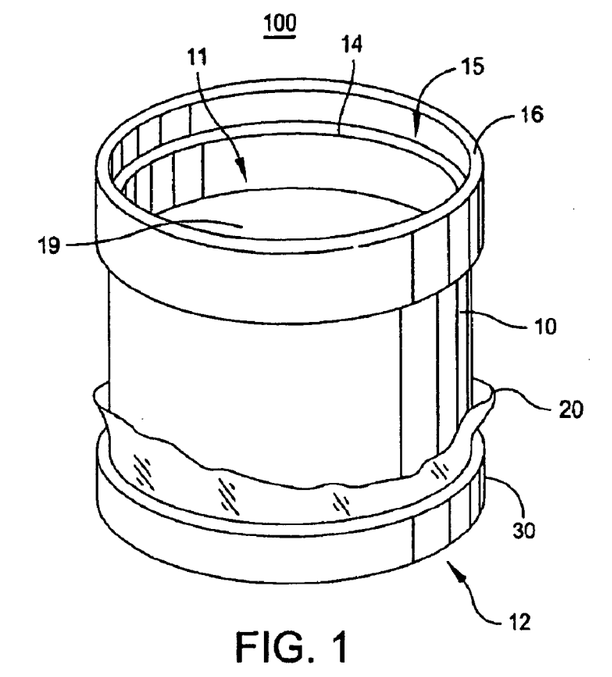
FIG. 1 is a perspective view of a sample cup according to an embodiment of the present invention.
Figure 2:
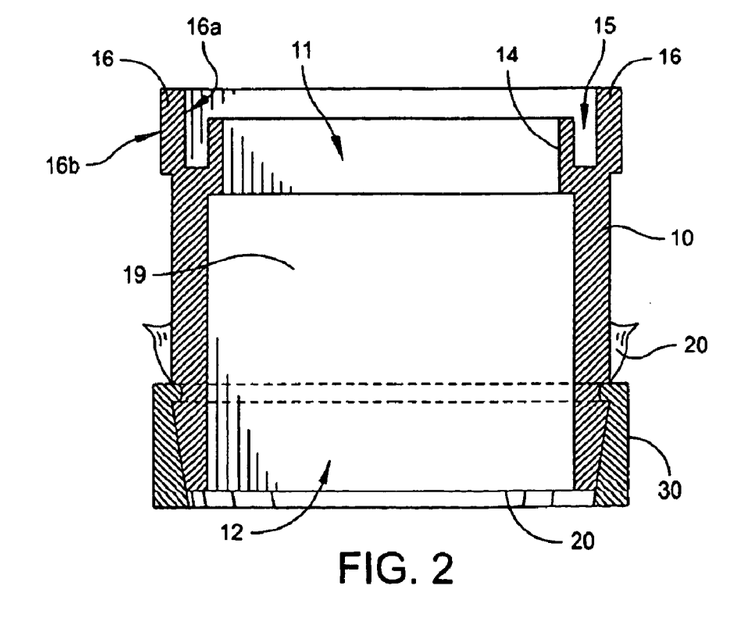
FIG. 2 is a cross-sectional view of the sample cup of FIG. 1.

Referring to FIGS. 1 and 2, there is shown a perspective view of assembled sample cup 100 for x-ray spectroscopy according to an embodiment of the present invention. The sample cup 100 comprises a cell body 10 of a cylindrical configuration. The cell body 10 has an open top end 11 and a bottom end 12. The bottom end 12 of the cell body 10 is an open structure but when assembled into a sample cup 100 as illustrated in FIGS. 1 and 2, the bottom end 12 is closed by a thin film sheet 20 of polymeric material secured and held in place around the bottom end 12 by a snap-on retaining ring 30. The cell body 10 and the thin film sheet 20 define a hollow 19 inside the sample cup 100 for holding a spectroscopy sample material (not shown). The top end 11 of the cell body 10 is configured to have an inner wall 14 and an outer wall 16 encircling the open top end 11. The inner wall 11 and the outer wall 16 extend axially and are positioned concentrically with respect to one another with a spacing therebetween, thus forming a reservoir space 15 between them. The outer wall 16 has an inner surface 16a and an outer surface 16b. The assembled sample cup 100 has a hollow space 19 defined by the cell body 10 and the thin film sheet 20 for holding the spectroscopy sample material (not shown).

Because the sample cup 100 is open at the top end 11, the spectroscopy sample may be introduced into the hollow space 19 through the top end opening after the bottom end 12 is closed by the thin film sheet 20.

Figure 3:
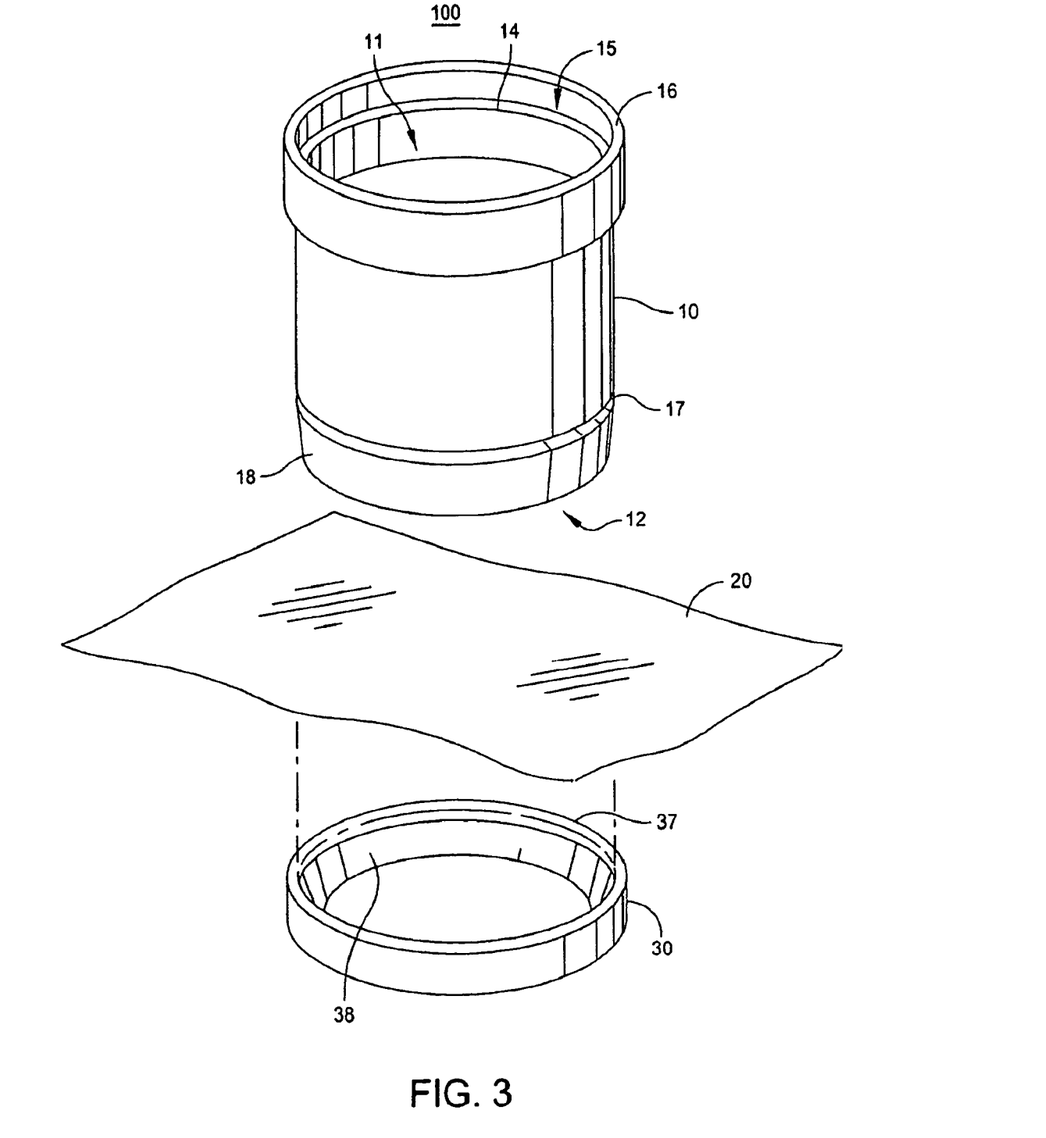
FIG. 3 is an assembly view of the sample cup of FIG. 1.
Figure 4:
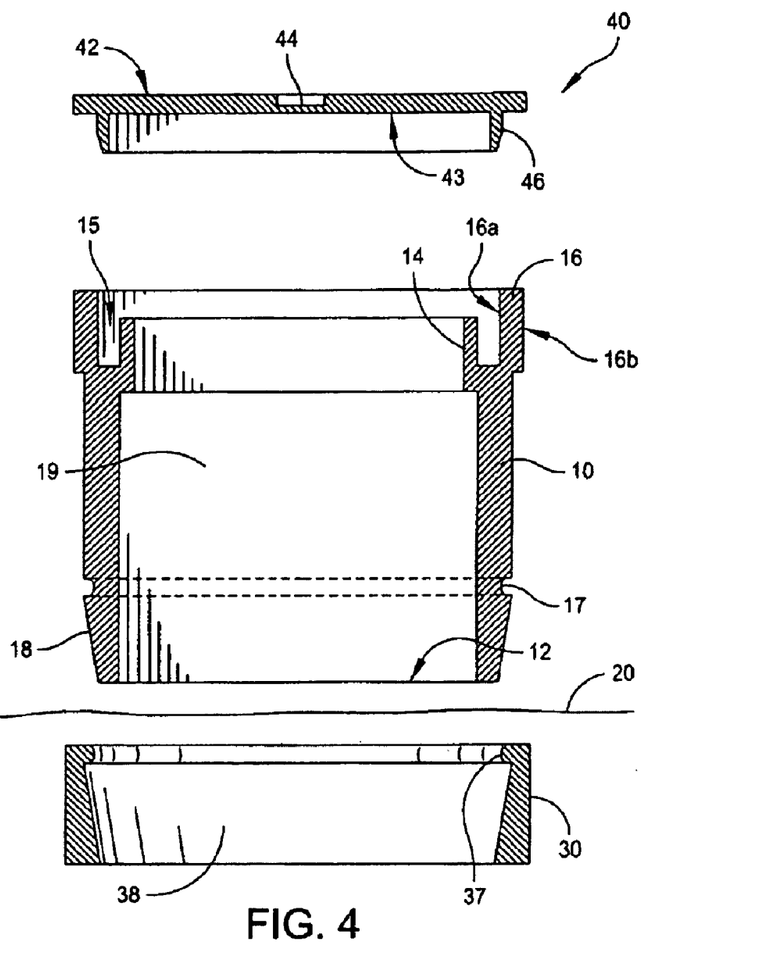
FIG. 4 is a cross-sectional view of the sample cup assembly of FIG. 3 including an optional cap.

Referring to FIGS. 3 and 4, a perspective assembly view and a cross-sectional assembly view of the sample cup 100 are shown, respectively. The cell body 10 is a cylindrical structure having an open top end 11 and an open bottom end 12. The cell body 10 near its top end 11 is configured to have concentrically positioned inner wall 14 and an outer wall 16. Formed and defined by the inner wall 14 and the outer wall 16 is a reservoir space 15. On the exterior surface of the cell body 10 near the bottom end 12 is a peripheral groove 17 around the outer surface of the cell body 10 for accommodating the snap-on retaining ring 30. A bottom collar portion 18 between the peripheral groove 17 and the bottom end 12 of the cell body 10 is tapered to allow for easy insertion of the snap-on retaining ring 30.

The snap-on retaining ring 30 has an inwardly extending peripheral ridge 37 about a top opening and adapted to cooperate with the peripheral groove 17 on the cell body 10. When the snap-on retaining ring 30 is placed over the bottom end 12 of the cell body and slid over the bottom collar portion 18, the peripheral ridge 37 snaps into the peripheral groove 17. The inner surface 38 of the snap-on retaining ring 30 is tapered to match the taper of the bottom collar portion 18 of the cell body 10.

To close or seal the bottom end 12 of the cell body 10, a thin film sheet 20 is placed over the open bottom end 12 and held in place by sliding the snap-on retaining ring 30 over the bottom collar portion 18 until the ridge 37 of the snap-on retaining ring 30 snapingly engages the peripheral groove 17. The snapping engagement between the internal ridge 37 of the snap-on retaining ring 30 and the peripheral groove 17 of the cell body grips the thin film sheet 20 in sufficient manner to maintain a flat sample plane necessary for the spectrochemical analysis.

The thin film sheet 20 may be a polymer sheet, such as MYLAR, that is transparent to the radiant energy used in the spectrochemical analysis. The possible compositions of such thin film materials are well known in the art and need not be set forth herein at length, but polyethylene is an example.

Figure 5:
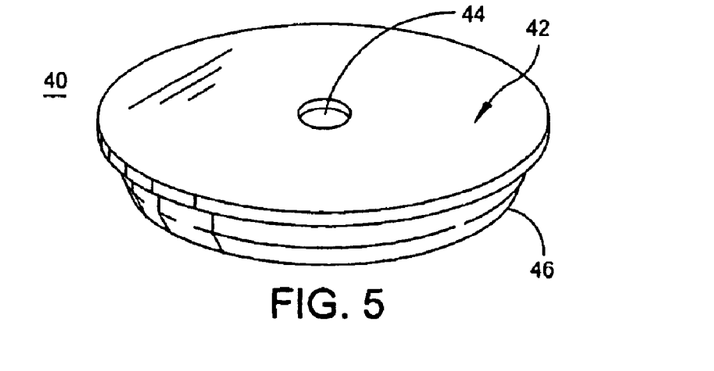
FIG. 5 is a perspective view of the cap shown in FIG. 4.

In an another embodiment of the present invention, the sample cup 10 may also include a cap 40 as illustrated in FIGS. 4 and 5. The cap 40 is a substantially a disc-like structure having a top surface 42 and a bottom surface 43. Extending downwardly from the bottom surface 43 is a sidewall 46. As illustrated, the sidewall 46 is peripherally located on the bottom surface 43 of the cap 40. The sidewall 46 is configured and dimensioned to frictionally fit against the inner surface 16a of the outer wall 16 of the cell body 10. For example, to achieve the frictional fit, the sidewall 46 may have a tapered outer surface whose diameter near the base of the sidewall 46 (i.e., near the bottom surface 43 of the cap 40 is at its greatest and is slightly larger than the diameter of the inner surface 16a of the outer wall 16 of the cell body 10. Thus, when the cap 40 is pressed into the top end 11 of the cell body 10, the tapered outer surface of the sidewall 46 frictionally engages the inner surface 16a and securely holds the cap 40 in place. The cap 40 may also be provided with an optional vent 44. The vent 44 is a portion of the cap 40 that is intentionally made thin so that the thin portion can be punctured using a sharp object creating a vent hole. This feature is useful when an equalization of the pressures between the inside and the outside of the sample cup 100. Alternatively, a thin polymer film sheet may be used to close the top end.

Figure 8:
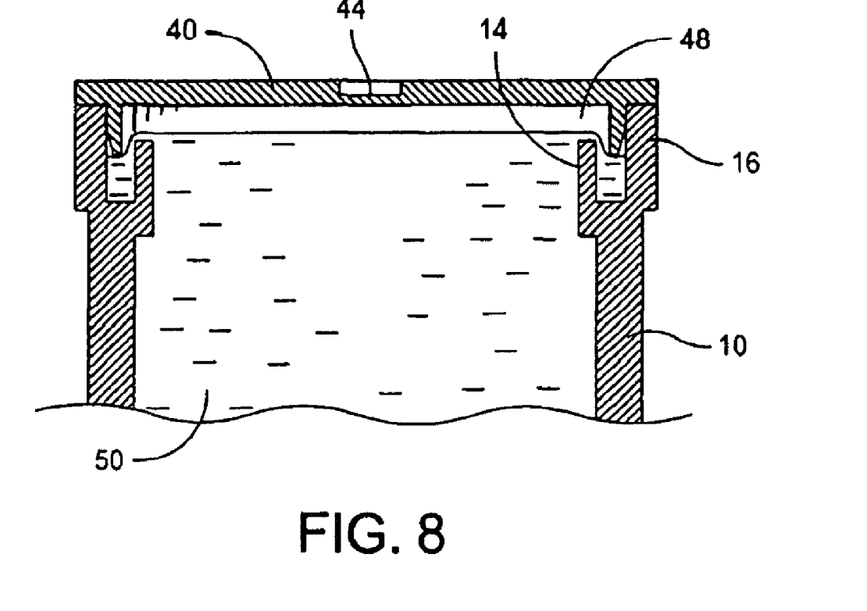
FIG. 8 is a partial view of a cross-sectional view of the sample cup according to another embodiment of the present invention.

By adjusting the height of the inner wall 14, the sample cup 100 may be customized to adjust the amount of volume expansion of a sample material that is required before the sample material overflows from the internal hollow 19 of the sample cup 100 into the reservoir space 15. As illustrated in FIG. 8, in a preferred embodiment of the present invention, the inner wall 14 may be sufficiently shorter than the outer wall 16 in order to maintain some space 48 between the cap 40 and the inner wall 14 when a cap is used. But the specific dimensions of the inner wall 14, the outer wall 16 and spacing between the two walls may be configured and adjusted according to the particular size of the reservoir space 15 that is desired for a given application.

Figure 6:
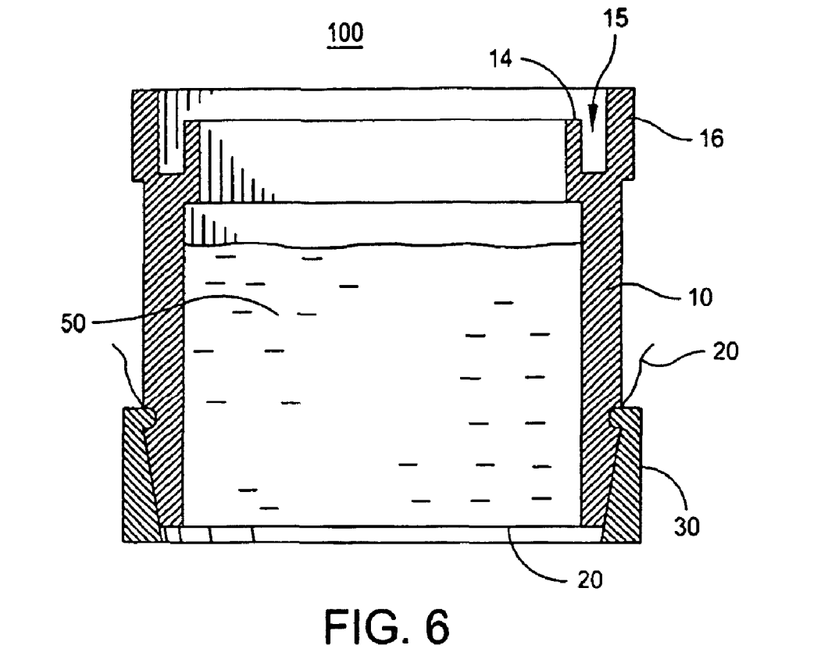
FIG. 6 is a cross-sectional view of the sample cup of FIG. 1 with a sample material inside the sample cup.
Figure 7:
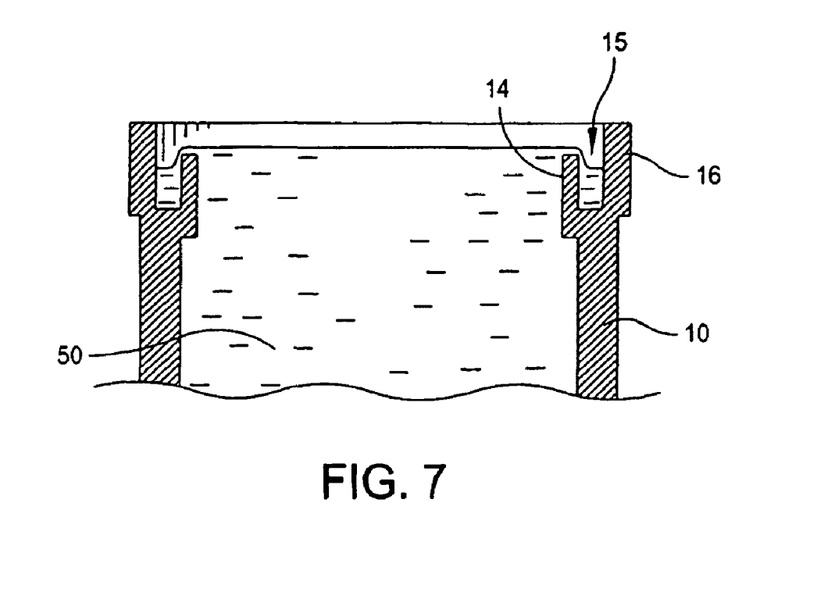
FIG. 7 is a partial view of the cross-sectional view of FIG. 6 in which the sample material is overflowing into the reservoir space of the sample cup.

Referring to FIGS. 6 and 7, the function of the reservoir space 15 according to the present invention is illustrated. In FIG. 6, a cross-sectional view of a sample cup 100 containing a liquid sample material 50 (e.g. oil) is shown. During an x-ray spectroscopy, the liquid sample material 50 is heated from excitation by the x-ray energy. As the liquid sample material 50 gets hotter, it expands in volume and the liquid sample material 50 will rise inside the sample cup 100. As illustrated in FIG. 7, if the volume expansion of the liquid sample material 50 is sufficiently large, the liquid sample material 50 will rise above the inner wall 14 and flow over. But the reservoir space 15 is sufficiently large to accommodate the over flowing liquid sample material 50 and prevent it from over flowing into the x-ray spectroscopy chamber.

All components of the sample cup 100 may be fabricated from an appropriate polymer such as polyethylene.

Figure 9:
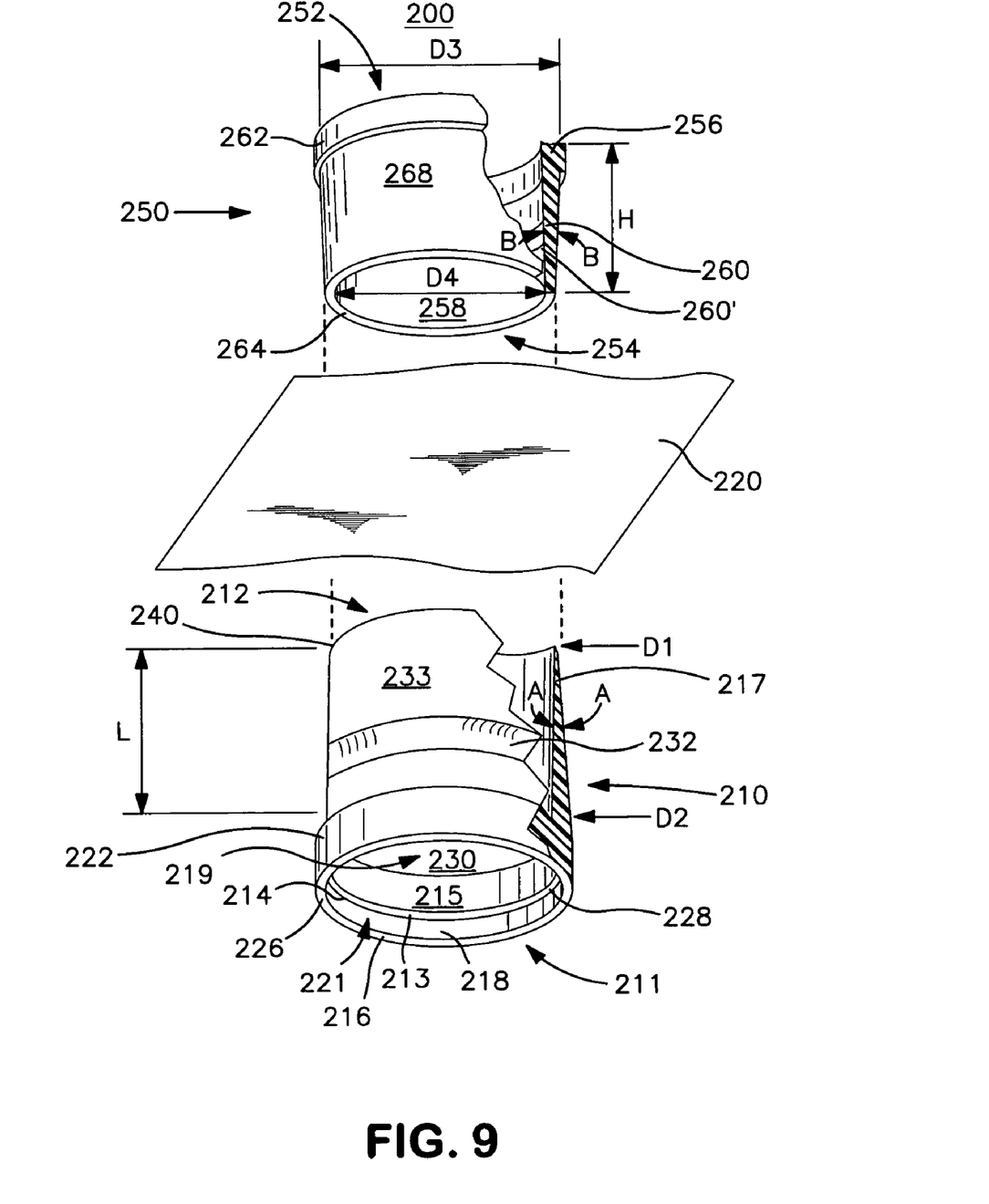
FIG. 9 is an exploded view of a sample cup according to another aspect of the invention.

Referring to FIG. 9, there is shown an alternative embodiment of a sample cup assembly 200 according to an aspect of the present invention. In FIG. 9, the assembly 200 is shown in an inverted, pre-assembled state to illustrate a method by which the components of the assembly 200 may be assembled. As illustrated, the sample cup assembly 200 includes a main cell body 210, a sheet of thin film material 220, and an annular collar 250 designed to secure the thin film material 220 over the cell body 210 and to close the open bottom end 212 of the cell body 210.

Figure 10:
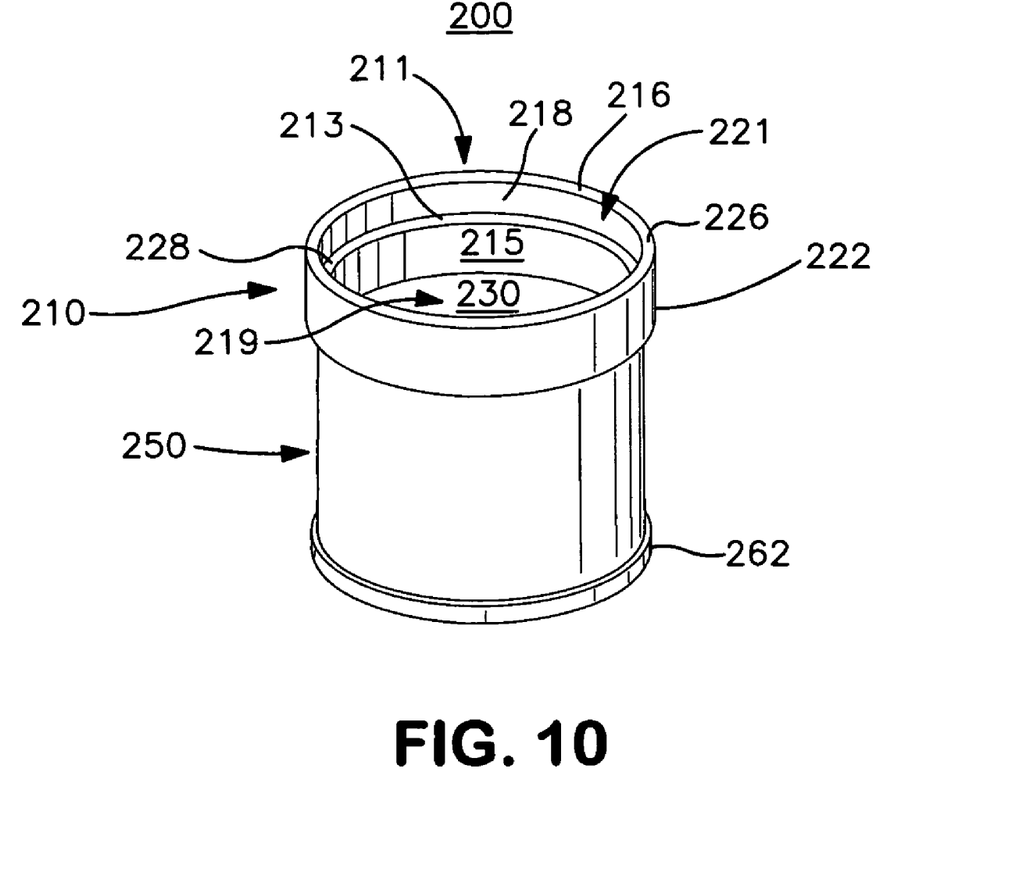
FIG. 10 is an elevational view of an assembled sample cup illustrated in FIG. 9 according to another aspect of the invention.

Referring to FIGS. 9 and 10, the cell body 210 includes a sample retaining region or hollow 219 and an internal reservoir space 221 for receiving overflow of a heat-sensitive sample from the hollow 219. The cell body 210 includes an open top end 211 and an open bottom end 212. The cell body 210 also includes an inner wall 213 and an outer wall 216, both located adjacent the open top end 211. Cell body further includes a tapered wall portion 217.

Adjacent the open top end 211, the inner wall 213 includes an outer surface 214 and an inner surface 215. The inner surface 230 of the cell body 210 located below the internal reservoir space 221 defines a hollow 219 for retaining a sample specimen. The inner wall 213 of the cell body 210 is substantially cylindrical and extends in a substantially vertical direction from the interface of the internal reservoir space 221 with the hollow 219 toward the open top end 211 of the cell body 210.

The tapered wall portion 217 of the cell body 210 is tapered at an angle of inclination A. The tapered wall portion 217 tapers outwardly from the open bottom end 212 to the interface of the hollow 219 and the internal reservoir space 221 adjacent the open top end 211 of the cell body 210. As illustrated, tapered wall portion 217 has a first diameter D1 at the open bottom end 212 that is less than the second diameter D2 proximate the open top end 211 of the cell body 210. The tapered wall portion 217 ends at the interface of the hollow 219 and the internal reservoir space 221. The cell body 210 may further include a peripheral flange 222 proximate the open top end 211. The open bottom end 212 of cell body 210 may also include a rounded edge 240 to prevent tearing, stretching or wrinkling of the film material 220 upon assembly.

Still referring to FIG. 9, a sheet of thin film material 220 is positioned between the open bottom end 212 of a cell body 210 and an annular collar 250. The thin film material 220 is flexible and transparent to the radiant energy used in spectrochemical analysis. The possible compositions of thin film materials 220 are well known in the art and need not be set forth herein at length, but polyethylene, ETNOM, PROLENE, and MYLAR are suitable examples.

Annular collar 250 is used to properly position the thin film material 220 across the open bottom end 212 of the cell body 210. The annular collar 250 is substantially cylindrical and has an open top end 252 and an open bottom end 254. The wall 256 of the annular collar 250 is tapered at an angle of inclination B that is supplementary to the angle of inclination A of the tapered wall portion 217 of cell body 210. Wall 256 tapers outwardly from the open bottom end 254 to the open top end 252. As illustrated, the first inner diameter D3 of the annular collar 250 proximate the open top end 252 is larger than the second inner diameter D4 proximate the open bottom end 254.

A rounded bottom edge 264 proximate the open bottom end 254 may be formed on the interior of the annular collar 250. The rounded shape of the bottom edge 264 prevents the thin film material 220 from being torn by the annular collar 250 during assembly of the sample cup 200. One or more continuous semicircular protrusions or beads 260 and 260' extending outwardly from the inner surface 258 of wall 256 may be formed on the annular collar 250. The bead, 260 or 260', or beads 260 and 260', provide a means for gripping the thin film material 220 and facilitate the placement of the thin film material 220 between the annular collar 250 and the cell body 210 upon assembly. The beads 260 and 260' are adapted to matingly engage with an external groove 232 (FIG. 9) which may also be formed on the cell body 210 (or 210' illustrated in FIG. 13).

A peripheral extension or flange 262 may be formed on the exterior wall surface 268 of the annular collar 250 adjacent the open top end 252 thereof according to an aspect of the invention. The flange 262 facilitates the handling and the alignment of the overall sample cup 200 during assembly and the placement of the cup assembly 200 within the analysis chamber of spectroscopic instrumentation.

Referring to FIG. 9 (and FIG. 10 which illustrates an inverted and assembled sample cup 200), as the annular collar 250 is advanced over the cell body 210, the thin film material 220 covers the open bottom end 212 and becomes lodged between the outer wall surface 233 of the tapered wall portion 217 of the cell body 210, and the inner surface 258 of the wall 256 of the annular collar 250. As the open bottom end 254 of the annular collar 250 is placed over the open bottom end 212 of the cell body 210, an interference fit occurs between the annular collar 250, thin film material 220 and cell body 210. Upon further advancement of the annular collar 250, the thin film material 220 is pulled tautly across the open bottom end 212 of cell body 210. As the annular collar 250 is further advanced along the cell body 210, the thin film material 220 is pulled tautly over edge 240 of cell body 210.

As the annular collar 250 is advanced along the cell body 210, the interference fit of the inner wall surface 258 of the annular collar 250, the thin film material 220, and the outer wall surface 233 of the cell body 210 increases due to the tapered shapes of both the inner wall surface 258 of the annular collar 250 and the outer wall surface 233 of the cell body 210. As the forces of the interference fit increase, the tautness applied to the thin film material 220 increases, thereby eliminating any folds or wrinkles in the portion of the thin film material 220 that covers the open bottom end 212 of the cell body 210.

Upon assembly of the sample cup 200, the thin film material 220 is drawn tightly over the open top end 211 of the cell body 210, and closes or seals the open end. The thin film material 220 creates a seal across the open bottom end 212 and along the edge 240 of the cell body 210 which is impermeable to the sample contained therein.

The interference fit between the tapered inner wall surface 258 of the annular collar 250 and the tapered wall portion 217 of the cell body 210 occurs for substantially the entire length of the tapered surfaces to prevent the thin film material 220 covering the open end 212 of cell body 210 from loosening. Advantageously, the thin film material 220 will remain taut across the bottom end 212, creating a wrinkle-free sample surface plane for the spectrochemical analysis.

To the extent that any excess thin film material 220 extends beyond the closed open end 212 of the cell body 210, the excess film is compressed between the outer wall surface 233 of the tapered wall portion 217 and the inner wall surface 258 of the annular collar 250. Provided that an appropriate length of thin film material 220 is initially used, no portion of thin film material 220 will extend beyond the height of the annular collar 250. Thus, the step of having to trim extraneous portions of thin film material 220 away from the exterior of the sample cup assembly 200 is eliminated. As with the snap-on retaining ring of the previous embodiment, the annular collar 250 greatly simplifies sample preparation since the number of operational steps are reduced.

After the sample cup 200 is assembled, a sample substance may be placed in the cup 200. To introduce a sample substance, the cup 200 is inverted (as illustrated in FIG. 10), and a sample is introduced into the hollow 219. Sample substances contained within the sample cup assembly 200 will come into contact with the portion of thin film material 220 covering the open end 212 of the cell body 210. Thereafter, the sample-containing sample cup assembly 200 may be placed in an analysis chamber of a spectroscopic instrument to be subjected to spectrochemical analysis. It should be understood by those skilled in the art that the x-ray beams impinge upon the thin film material 220 during analysis.

Figure 11:
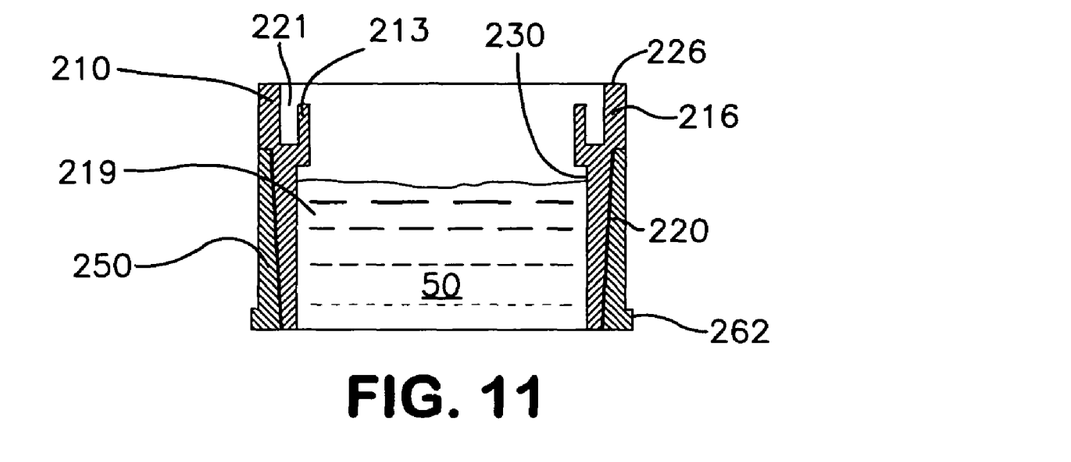
FIG. 11 is a cross-sectional view of the sample cup with a sample material contained therein according to another aspect of the invention.
Figure 12:
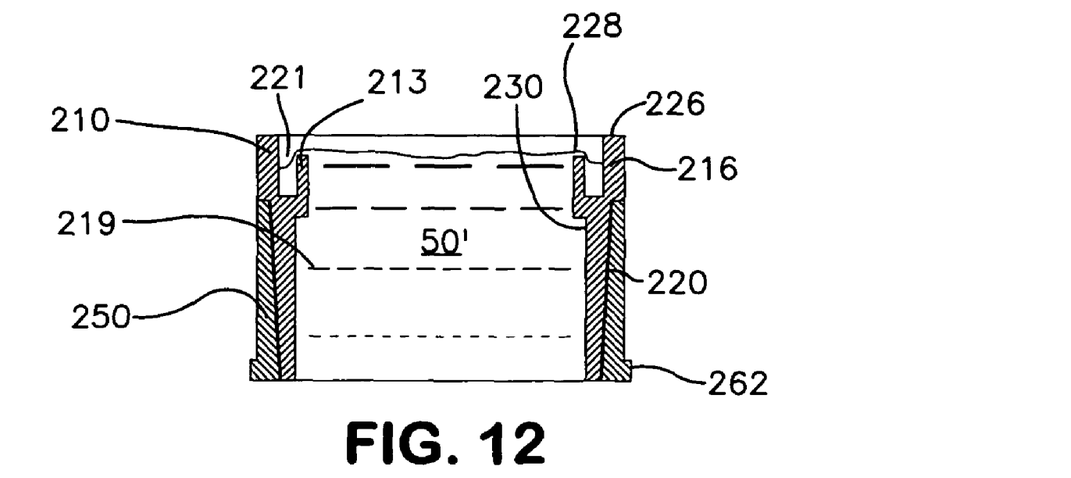
FIG. 12 is a cross-sectional view of the sample cup with sample material that has overflowed into the internal reservoir according to another aspect of the invention.

Referring to FIGS. 11 and 12, the function of the reservoir space 221 according to the present invention is illustrated. In FIG. 11, a cross-sectional view of an assembled sample cup 200 containing a liquid sample material 50 (e.g. oil) is shown. During spectroscopic analysis, the liquid sample material 50 is heated from excitation by the x-ray energy. As the liquid sample material 50 increases in temperature, it also expands in volume and the level will rise inside the sample cup assembly 200.

As illustrated in FIG. 12, the volume expansion of the liquid sample material 50' is greater than the volume that the hollow 219 can retain, and the liquid sample material 50' flows over the inner edge 228 of the inner wall 213 and downwardly into the internal reservoir space 221. The internal reservoir space 221 is sufficiently large enough to accommodate the overflowing liquid sample material 50', and the outer edge 226 of outer wall 216 prevents it from overflowing into an x-ray spectroscopy chamber.

Advantageously, if continuous venting is desired, the sample cup assembly 200 may be placed in an analysis chamber without a cap. Without a cap, the sample substance is always equalized to the pressure of the ambient environment. In applications where a liquid sample to be analyzed is heat-sensitive, and expands upon the application of heat, the internal overflow reservoir 221 provides a means to receive the overflow of liquid, as the volume of sample material may increase within the hollow 219 during analysis, flow over the edge 228 of the inner wall 213, and flow downwardly into the internal reservoir space 221. The upper edge 226 of the outer wall 216 prevents overflow of the liquid sample into the instrumentation chamber.

In some applications, for example, with powdered or liquid samples to be analyzed under evacuated conditions, additional resistance to sample withdrawal may be desired. In those applications, a cap may be placed on the open top end 211 of the sample cup assembly 220.

Figure 13:
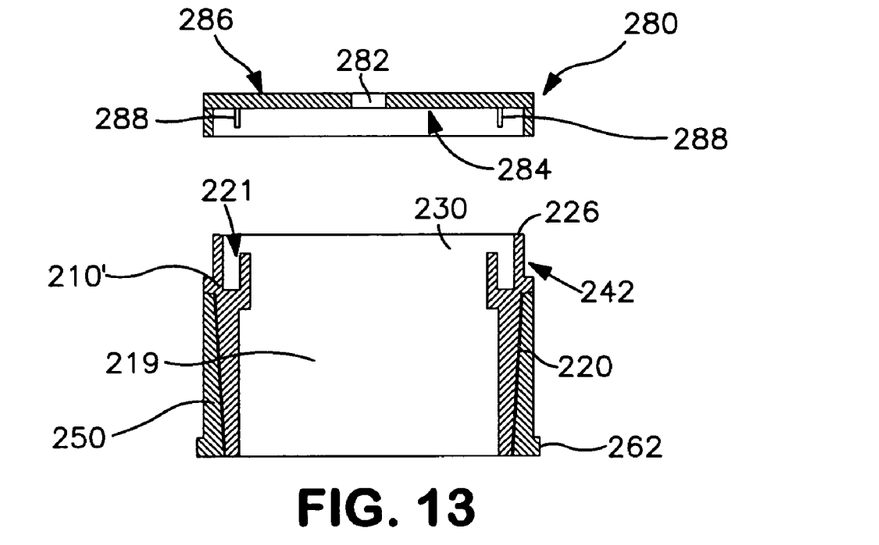
FIG. 13 is a cross-sectional view of the sample cup and a cap with a vent hole according to another aspect of the invention.
Figure 14:
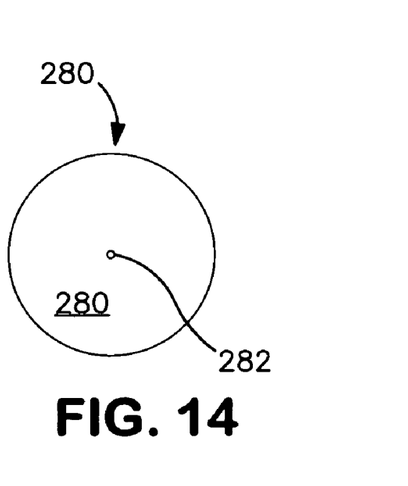
FIG. 14 is a top plan view of the cap illustrated in FIG. 13 according to another aspect of the invention.
Figure 15:
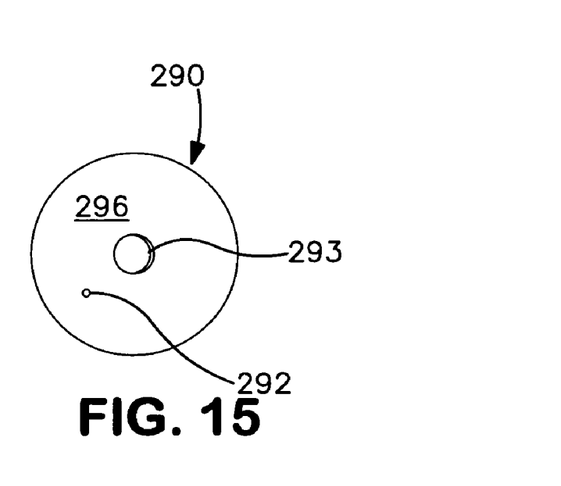
FIG. 15 is a top plan view of a cap with a vent hole and knob according to another aspect of the invention.
Figure 16:
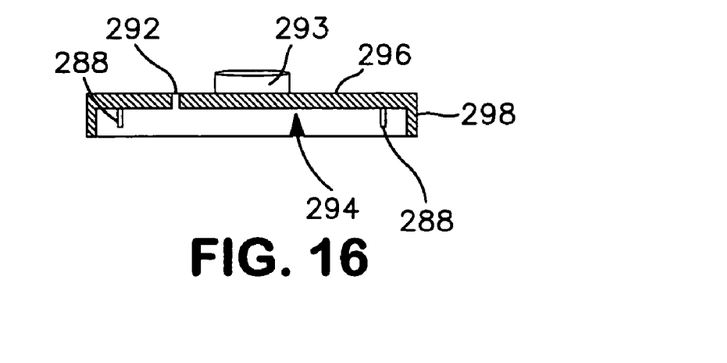
FIG. 16 is a cross-sectional view of the cap illustrated in FIG. 15 according to another aspect of the invention.

Referring to FIGS. 13-16, according to another aspect of the invention, suitable caps for placement on the sample cup assembly 200 are illustrated. FIG. 13 illustrates another aspect of the invention with a cell body 210' that includes an annular recess 242 on the outer wall surface 233 for receiving a cap 280 or cap 290. FIG. 14 illustrates the cap 280 in FIG. 13 with a vent hole 282. It should be understood that although the vent hole 282, as illustrated, is substantially in the center of the cap, the vent hole may be offset therefrom, as illustrated in FIG. 15. It should also be understood that although one vent hole is illustrated, more than one vent hole may be present in the cap 280 or 290. FIGS. 15 and 16 illustrate an alternative cap 290 that includes an offset vent hole 292 and a knob 293.

Each cap, 280 and 290, has a circular disk-like shape with an outer surface 286 or 296, an inner surface 284 (FIG. 13) or 294 (FIG. 16), and includes a peripheral wall 288 or 298 extending from the inner surface 284 or 294, respectively, of the cap. The inner surface of the peripheral walls of each cap 280 and 290 frictionally and continuously engages the annular recess 242 on the outer surface 233 of cell body 210' when disposed thereon. Extending from the inner surface, 284 or 294, may also be a ridge 288. The ridge 288 provides a tortuous path for overflowing sample material, and tends to slow down the flow thereof. Upon assembly, the ridge 288 is approximately equidistant from the inner wall 213 and outer wall 216 of the internal reservoir space 221. It should be understood that more than one ridge 288 may be present.

When using a cap, venting of gaseous fluids, including air, from the sample cup assembly 210' prevents the thin film material 220 from distending inwardly or outwardly under positive inert gas pressure and in evacuated conditions, respectively, and allows the portion of thin film material disposed across the open bottom end 212 of the cup to remain substantially planar.

Figure 17:
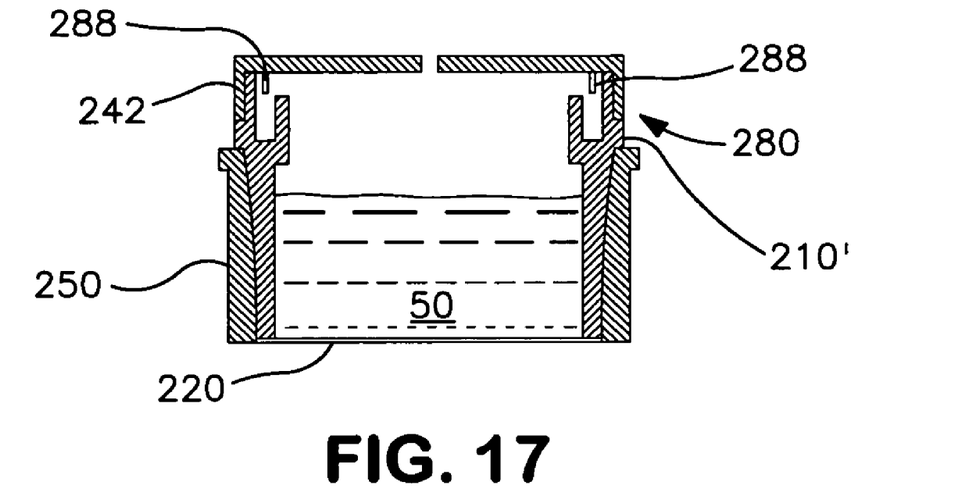
FIG. 17 is a cross-sectional view of the assembled sample cup and cap illustrated in FIG. 13, with sample material contained in the cup according to another aspect of the invention.
Figure 18:
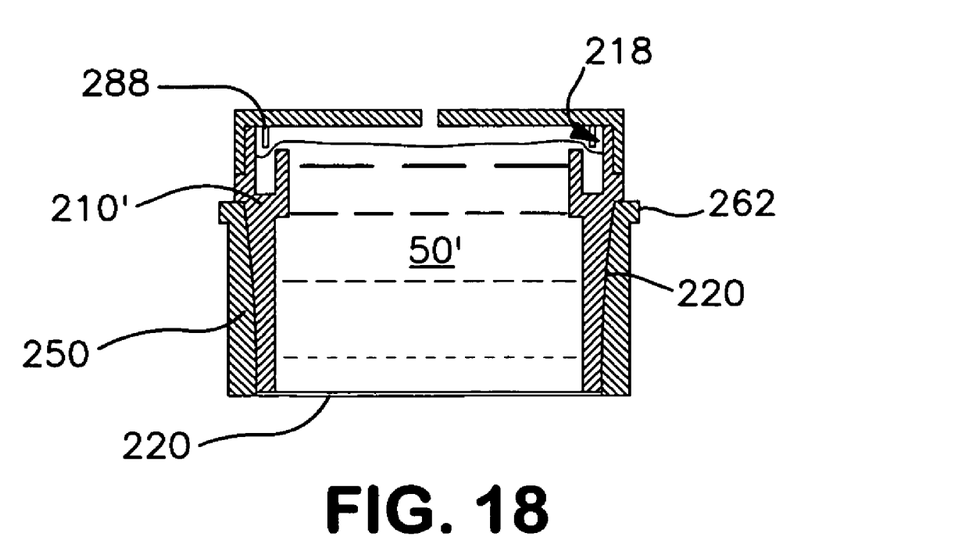
FIG. 18 is a cross-sectional view of the assembled sample cup and cap illustrated in FIG. 14, with expanded sample material that has overflowed into the internal reservoir according to another aspect of the invention.

Referring to FIGS. 17 and 18, the assembled sample cup is illustrated with an alternative arrangement of the annular collar 250' disposed on the cell body 210' with a cap 280 disposed thereon. Since it is open at each end, the annular collar 250' may be inverted for placement on cell body 210 or 210' to provide a satisfactory interference fit. Advantageously, inversion of the annular collar 250 to obtain an interference fit is possible due to the dimensions of the tapered portions of the components as the tapered portions are dimensioned to permit such inversion. Assembly with an inverted annular collar 250 may be desired in some instances. According to this aspect of the invention, the peripheral flange 222 of the cell body 210 or 210' acts as a "stop" to the flange 262 of the annular collar 250', to aid in the proper placement of the annular collar 250' on the cell body 210 or 210'. In one aspect of the invention, the annular collar 250 may have a vertical height H that is equal, or substantially equal, to that of the length L of the tapered wall portion 217 of the cell body 210.

The cell body and the annular collar may be fabricated from unrecycled natural polyethylene. This eliminates the potential possibility of introducing metallic contamination that may adversely affect the analysis of a sample substance. In addition to polyethylene, polycarbonate and polypropylene are exemplary materials that may be utilized due to the excellent mass attenuation properties encompassing the 1 to 12 Angstrom analyte wavelength range. In addition, the selected material should be resistant to chemical attack, temperature softening, and degradation from excitation energy sources, as well as exhibiting excellent tensile strength for adequate sample retention.

While the foregoing invention has been described with reference to the above embodiments, various modifications and changes can be made without departing from the spirit of the invention. Accordingly, all such modifications and changes are considered to be within the scope of the appended claims.

It should be understood that the various aspects of the present invention described herein are merely exemplary and that a person skilled in the art may make many variations and modifications to the described embodiment utilizing functionally equivalent components to those described. As such, variations and modifications, including differing physical geometries, proportions and materials are intended to be included within the scope of the invention as defined in the appended claims.

Benefits, other advantages, and solutions to problems have been described above with regard to specific embodiments. The benefits, advantages, solutions to problems and any element(s) that may cause any benefit, advantage, or solution to occur or become more pronounced are not to be construed as a critical, required, or essential feature or element of any or all of the claims.

What is claimed is:

1. A sample cup, comprising:
   a substantially cylindrical cell body comprising
      an open top end including an outer wall with an outer top edge and an inner wall with an inner top edge, said outer wall and said inner wall extending axially and positioned in a concentric relationship, said outer wall and said inner wall forming an internal reservoir space therebetween for receiving overflow of an expanded sample material;
      an open bottom end; and
      a hollow defined between said, open top end and said open bottom end for receiving a sample material capable of expansion during analysis, said top edge of said inner wall being positioned a selected distance below said outer top edge of said outer wall to allow said expanded sample material to flow downwardly over said inner top edge and said outer top edge prevents overflow of said expanded sample material out of said cell body; and
   a cap, comprising a top surface, a bottom surface, and a peripherally disposed sidewall extending downwardly from said bottom surface of said cap, said sidewall frictionally and continuously engaging said outer wall, wherein, upon assembly, said cap is coupled to said cell body and maintains a space between said bottom surface of said cap and said inner top edge of said inner wall.

2. The sample cup according to claim 1, further comprising:
   means for retaining a thin film material across said open bottom end of said cell body.

3. The sample cup according to claim 2, wherein the thin film material comprises a thin sheet of polymer stretched over the open bottom end; and the means for retaining comprises a snap-on retaining ring positioned about an outer edge of the cell body adjacent the open bottom end to hold the thin sheet of polymer in place.

4. The sample cup according to claim 2, wherein the thin film material comprises a thin sheet of polymer stretched : over the open bottom end; and the means for retaining comprises an annular collar positioned about an outer surface of the cell body to hold the thin sheet of polymer in place.

5. The sample cup according to claim 3, wherein the thin sheet of polymer is a polyester film.

6. the sample cup according to claim 4, wherein the thin sheet of polymer is a polyester film.

7. The sample cup according to claim 3, wherein the cell body has a peripheral groove around an outer surface thereof and located adjacent the open bottom end to cooperate with and retain the snap-on retaining ring.

8. The sample cup according to claim 7, wherein the snap-on retaining ring has an inwardly extending peripheral ridge about a top opening and adapted to cooperate with the peripheral groove on the cell body.

9. The sample cup according to claim 4, wherein the annular collar comprises a substantially cylindrical wall having an open top end and an open bottom end.

10. The sample cup according to claim 4, wherein the cell body and the annular collar are fabricated from a polymer material.

11. The sample cup according to claim 1, wherein the sample material is a thermally-sensitive liquid.

12. A sample cup assembly for retaining a specimen to be subjected to analysis, comprising:
    a substantially cylindrical cell body comprising:
       an open top end including an outer wall with an outer top edge and an inner wall with an inner top edge, said outer wall and said inner wall extending axially and positioned in a concentric relationship, said outer wall arid said inner wall forming an internal reservoir space therebetween for receiving overflow of an expanded sample material;
       an open bottom end; and
       a hollow defined between said open top end and said open bottom end for receiving a sample material capable of expansion during analysis, said inner top edge of said inner wall allowing said expanded sample material to flow downwardly over said inner top edge and said outer top edge preventing overflow of the expanded sample material out of the cell body;
    a cap, comprising a top surface, a bottom surface, and a peripherally disposed sidewall extending downwardly from said bottom surface of said ca said sidewall frictionally and continuously engaging said outer wall, wherein, upon assembly, said cap is coupled to said cell body and maintains a space between said bottom surface of said cap and said inner to a edge of said inner wall;
    a thin film of material disposed across said open bottom end; and
    means for retaining the thin film of material tautly across said open bottom end.

13. The sample cup assembly according to claim 12, wherein the cap includes a vent hole for allowing gaseous fluids to escape.

14. The sample cup assembly according to claim 12, wherein the means for retaining the thin film of material comprises a snap-on retaining ring positioned about an outer edge of the cell body adjacent the open bottom end to hold the thin sheet of polymer in place.

15. The sample cup assembly according to claim 12, wherein the means for retaining the thin film of material comprises an annular collar positioned about an outer surface of the cell body to hold the thin sheet of polymer in place.

16. The sample cup assembly according to claim 12, wherein the thin sheet of polymer is a polyester film.

17. The sample cup assembly according to claim 15, wherein the annular collar comprises a substantially cylindrical wall having an open top end and an open bottom end.

18. The sample cup assembly according to claim 12, wherein the sample material is a thermally-sensitive liquid.

19. A method for spectroscopically analyzing a sample material, comprising the steps of:
- disposing a sample material into a sample cup comprising:
  - a substantially cylindrical cell body comprising
    - an open top end including an outer wall with an outer top edge and an inner wall with an inner top edge, said outer wall and said inner wall extending axially and positioned in a concentric relationship, said outer wall and said inner wall forming an internal reservoir space therebetween for receiving overflow of an expanded sample material;
    - an, open bottom end;
    - a hollow defined between said open top end and said open bottom, end for receiving a sample material capable of ;expansion during analysis, said inner wall allowing said expanded sample material to flow downwardly over said inner top edge and said outer top edge preventing overflow of the expanded sample material out of the cell body;
- disposing a thin film of material across said open bottom end; and
- providing a means for retaining the thin film of material tautly across said open bottom end;
- disposing a cap onto said open top end of said cell body, said cap comprising a top surface, a bottom surface, and a peripherally disposed sidewall extending downwardly from said bottom surface of said cap, said sidewall frictionally and continuously engaging said outer wall, wherein, upon assembly, said cap is coupled to said cell body and maintains a space between said bottom surface of said cap and said inner top edge of said inner wall; and
- subjecting the sample material to spectroscopic analysis.

* * * * *

UNITED STATES PATENT AND TRADEMARK OFFICE
CERTIFICATE OF CORRECTION

PATENT NO.         : 8,043,862 B2                                                    Page 1 of 1
APPLICATION NO.    : 12/925048
DATED              : October 25, 2011
INVENTOR(S)        : Monte J. Solazzi It is certified that error appears in the above-identified patent and that said Letters Patent is hereby corrected as shown below:

In Claim 1, column 11, line 37, delete the "," as follows: said [,] open.
In Claim 1, column 11, line 39, insert the word --inner-- as follows: said inner top edge.
In Claim 4, column 11, line 64, delete the ":" as follows: stretched [:].
In Claim 6, column 12, line 3, delete the first occurrence of "the" and replace with The.
In Claim 12, column 12, line 42, delete "ca" and replace with cap.
In Claim 12, column 12, line 46, delete "to a" and replace with top.

Signed and Sealed this
Seventh Day of February, 2012

David J. Kappos
*Director of the United States Patent and Trademark Office*